United States Patent
Kremminger et al.

(10) Patent No.: US 9,096,610 B2
(45) Date of Patent: Aug. 4, 2015

(54) METHOD FOR THE PRODUCTION OF CEFTOBIPROLE MEDOCARIL

(75) Inventors: Peter Kremminger, Kundl (AT);
Johannes Ludescher, Kundl (AT);
Hubert Sturm, Kundl (AT)

(73) Assignee: SANDOZ AG, Basel (CH)

( * ) Notice: Subject to any disclaimer, the term of this patent is extended or adjusted under 35 U.S.C. 154(b) by 0 days.

(21) Appl. No.: 13/320,414

(22) PCT Filed: May 25, 2010

(86) PCT No.: PCT/EP2010/057104
§ 371 (c)(1),
(2), (4) Date: Jan. 20, 2012

(87) PCT Pub. No.: WO2010/136422
PCT Pub. Date: Dec. 2, 2010

(65) Prior Publication Data
US 2012/0116070 A1    May 10, 2012

(30) Foreign Application Priority Data
May 25, 2009    (EP) ................................. 09161028

(51) Int. Cl.
*C07D 501/56*    (2006.01)
*C07D 501/04*    (2006.01)
*C07D 501/18*    (2006.01)

(52) U.S. Cl.
CPC ............ *C07D 501/56* (2013.01); *C07D 501/04* (2013.01); *C07D 501/18* (2013.01)

(58) Field of Classification Search
CPC .................................................. C07D 501/34
USPC ........................................ 540/214, 219, 228
See application file for complete search history.

(56) References Cited

U.S. PATENT DOCUMENTS

| | | | | |
|---|---|---|---|---|
| 6,384,214 B1 * | 5/2002 | Spurr et al. | ................... | 540/222 |
| 6,504,025 B2 * | 1/2003 | Hebeisen et al. | ............. | 540/222 |

FOREIGN PATENT DOCUMENTS

| | | | | |
|---|---|---|---|---|
| EP | 0037380 A2 | 10/1981 | | |
| EP | 0841339 A1 | 5/1998 | | |
| EP | 0849269 A | 6/1998 | | |
| EP | 0849269 A1 * | 6/1998 | ........... | C07D 501/35 |
| EP | 1067131 A1 | 1/2001 | | |
| EP | 1087980 B | 1/2003 | | |
| WO | 9529182 A | 11/1995 | | |
| WO | WO 95/29182 | * 11/1995 | ........... | C07D 501/18 |
| WO | 9965920 | 12/1999 | | |
| WO | WO 0104127 A1 * | 1/2001 | ........... | C07D 501/56 |
| WO | 0190111 A1 | 11/2001 | | |
| WO | 0214332 | 2/2002 | | |

OTHER PUBLICATIONS

Van Look, Gert. Silylating Agents. Fluka Chemika AG. Switchzerland. 1995.*
Greene, Theodora W. Greene's Protective Groups in Organic Synthesis 4th ed. Ch. 5 and 7. John Wiley & Sons, Inc. New Jersey. 2007.*
Kocienski, Philip J. Protecting Groups 3rd ed. Thieme. Germany. 2005.*
International Search Report and Written Opinion (mailed Jul. 26, 2010).
Current Opinion in Pharmacology 2006, 6, 480-485.
J. Antibiotics 37:557-571, 1984.
Yakugaku Zasshi 110 (9) 658-664, 1990, New Drug Research Laboratories, Fujisawa Pharmaceutical Co., Ltd., 2-1-6 Kashima, Yodagawa-ku, Osaka 532, Japan, NII-Electronic Library Services.
Fluka, 1995, Fluka Chemi AG, CH-9471, Switzerland, pp. 1-45.

* cited by examiner

*Primary Examiner* — Golam M M Shameem
*Assistant Examiner* — Laura Daniel
(74) *Attorney, Agent, or Firm* — Jeffrey S. Melcher; Manelli Selter PLLC

(57) ABSTRACT

The present invention relates to a method for the production of organic compounds, in particular sodium (6R,7R)-7-[(Z)-2-(5-amino-[1,2,4]thiadiazol-3-yl)-2-hydroxyimino-acetylamino]-8-oxo-3-[(E)-(R)-1'-(5-methyl-2-oxo-[1,3]-dioxol-4-ylmethoxycarbonyl)-2-oxo-[1,3']bipyrrolidinyl-3-ylidenemethyl]-5-thia-1-aza-bicyclo[4.2.0]oct-2-ene-2-carboxylate (ceftobiprole medocaril), and compounds of the general formula (1) and of the general formula (2), the compounds themselves and intermediates in the production according to the invention.

8 Claims, No Drawings

METHOD FOR THE PRODUCTION OF CEFTOBIPROLE MEDOCARIL

CROSS-REFERENCE TO RELATED APPLICATIONS

This application is a national stage entry under 35 U.S.C. 371 of International Application No. PCT/EP2010/057104, filed 25 May 2010, designating the U.S. This application claims foreign priority under 35 U.S.C. 119 and 365 to European Patent Application No. 09161028.7, filed 25 May 2009.

FIELD OF THE INVENTION

The present invention relates to a method for the production of organic compounds, in particular sodium (6R,7R)-7-[(Z)-2-(5-amino-[1,2,4]thiadiazol-3-yl)-2-hydroxyimino-acetylamino]-8-oxo-3-[(E)-(R)-1'-(5-methyl-2-oxo-[1,3]-dioxol-4-ylmethoxycarbonyl)-2-oxo-[1,3']bipyrrolidinyl-3-ylidenemethyl]-5-thia-1-aza-bicyclo[4.2.0]oct-2-ene-2-carboxylate (ceftobiprole medocaril), and compounds of the general formula (1) and of the general formula (2), the compounds themselves and intermediates in the production according to the invention. Ceftobiprole medocaril is a parenteral cephalosporin with outstanding antibacterial properties. An overview is given in, for example, Current Opinion in Pharmacology 2006, 6, 480-485.

BACKGROUND OF THE INVENTION

Methods for the production of ceftobiprole medocaril are known per se. The methods known from the prior art have the common feature that starting from 7-aminocephalosporanic acid, a large number of intermediate stages have to be isolated and purified in order to obtain ceftobiprole medocaril of the general formula (1) in a sufficient purity.

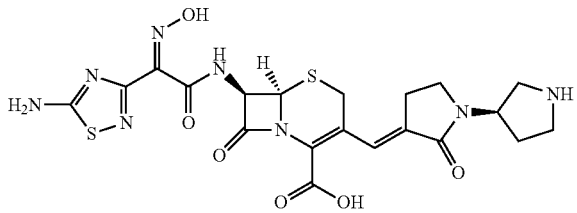

(2)

The compound of the general formula (2) is likewise known per se and has been described, for example, in EP 0 849 269 A1. According to EP 0 849 269 A1, the production of the compound of the general formula (2) is carried out starting from (2R,6R,7R)-tert-butoxycabonylamino-3-formyl-8-oxo-5-thia-1-azabicyclo[4.2.0]oct-3-ene-2-carboxylic acid benzhydryl ester by a Wittig reaction with (1'-allyloxycarbonyl-2-oxo-[1,3']bipyrrolidinyl-3-yl)-triphenylphosphonium bromide. The Δ2 reaction product formed in this reaction is isomerized back into the desired Δ3 isomer by sulfoxidation and subsequent reduction, and thereafter deprotected from the benzhydryl ester with trifluoroacetic acid. The acylation in position 7 is carried out by reaction with (Z)-(5-amino-[1,2,4]-thiadiazol-3-yl)-trityloxyiminothioacetic acid S-benzothiazol-2-yl ester. The compound of the general formula (2) is subsequently obtained by splitting off the protective groups.

EP 1 067 131 A1 describes the formation of the ylide in toluene or a mixture of toluene and methylene chloride by addition of alkali metal tert-butylate in tetrahydrofuran, by which means the base can be added as a solution. The reaction of the ylide with the corresponding aldehyde at a reaction temperature of −70° C. is described.

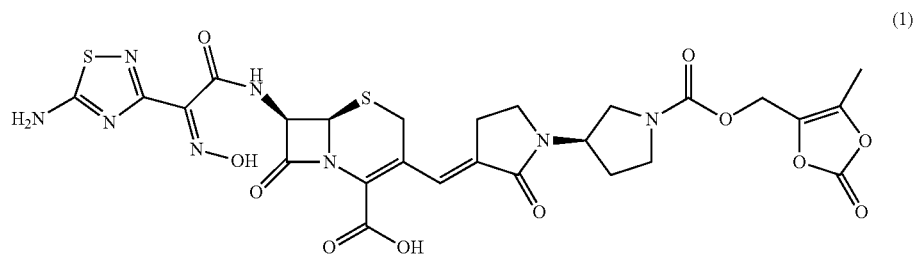 [SMILES: Cc1oc(=O)oc1COC(=O)N1CC[C@@H](N2CC/C(=C\C3=C(C(=O)O)N4C(=O)[C@@H](NC(=O)/C(=N\O)c5nsc(N)n5)[C@H]4SC3)C2=O)C1]

(1)

The compound of the general formula (1) is known per se and is described, for example, in WO 99/65920. It can be used for treatment and for prophylaxis of bacterial infectious diseases, in particular infectious diseases which are caused by methicillin-resistant *Staphylococcus aureus* strains.

WO 99/65920 describes, as the last step of the production process of ceftobiprole medocaril, a reaction in which the medocaril prodrug unit is introduced into a compound of the general formula (2).

EP 0 841 339 A1 relates to cephalosporin derivatives and methods for the production thereof. WO 95/29182 likewise discloses intermediate products for the production of cephalosporins.

WO 01/90111 describes a further production of ceftobiprole medocaril in several stages starting from deacetyl-7-aminocephalosporanic acid by acylation with (Z)-(5-amino-[1,2,4]-thiadiazol-3-yl)-trityloxyiminothioacetic acid S-benzothiazol-2-yl ester in N,N-dimethylformamide, followed by in situ esterification with diphenyldiazomethane in methylene chloride to give the corresponding benzhydryl ester, which is precipitated by addition of hexane and isolated. In the next step, this product is oxidized with TEMPO/NaOCl in methylene chloride/water or with manganese dioxide in tetrahydrofuran/methylene chloride to give the corresponding aldehyde. The next reaction step comprises the Wittig reaction to give the 3-vinyl-substituted derivative, in which the reaction is carried out in methylene chloride/toluene/tetrahydrofuran at −78° C. The crude product is extracted by stirring with ethanol and recrystallized from methylene chloride/tert-butyl methyl ether or purified by chromatography. According to the method disclosed in WO 01/90111, the Wittig reaction is carried out at low temperatures of from −80 to −70° C. in a complex solvent mixture of methylene chloride, toluene and tetrahydrofuran. When the reaction is carried out on a production scale, this leads to considerable disadvantages, since regeneration of the process solvents is made difficult.

A disadvantage of the syntheses known from the prior art is that the compound of the general formula (2) or of the general formula (1) is produced via a multi-stage process which comprises complex synthesis steps and delivers poor overall yields. Furthermore, involved protective group operations are necessary.

SUMMARY OF THE INVENTION

It has now been found, surprisingly, that compounds of the general formula (1) and of the general formula (2) can be produced via a method which can be carried out with few stages, even on an industrial scale.

Unless explicitly stated, the following statements in the context of the present invention in each case relate to the said compounds themselves and pharmaceutically acceptable salts thereof.

Objectives of the invention are obtained by a method for the production of a compound of the formula (1)

wherein $Q_1$ and $Q_2$ independently of each other represents a silyl group or wherein $Q_1$ represents a hydrogen atom and $Q_2$ represents a silyl group, with a compound of the formula (4)

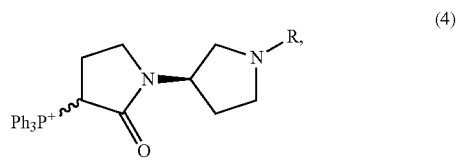

(4)

wherein R represents a 5-methyl-2-oxo-[1,3]-dioxo-1-4-yl-methoxycarbonyl group, to produce a compound of the formula (5)

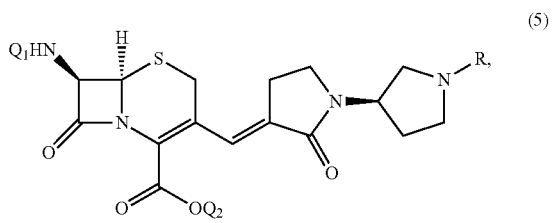

(5)

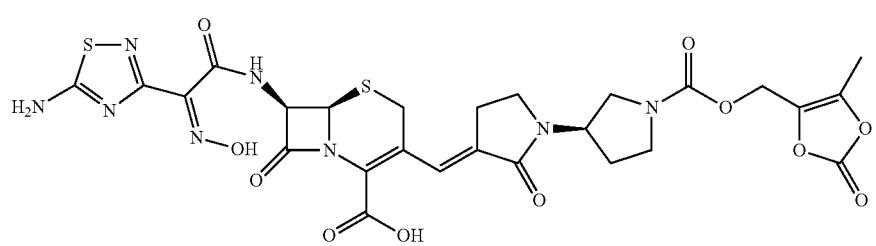

(1)

comprising at least the following steps (a) and (b):

(a) reacting a compound of the formula (3)

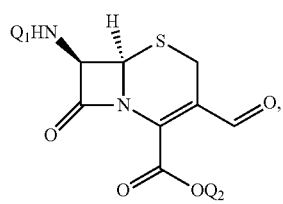

(3)

and (b) reacting the compound of the formula (5) with a compound of the formula (6)

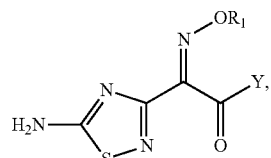

(6)

wherein $R_1$ represents a hydroxy-protective group and Y represents an activating functionality, wherein after removal of the protective group, if $Q_1$ represents a silyl group, to produce a compound of the formula (7)

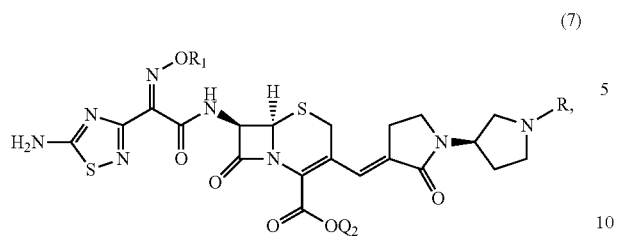

(7)

and optionally (c) converting the compound of the formula (7) into the compound of the formula (1).

Objectives of the invention are also obtained by a compound of the formula (5)

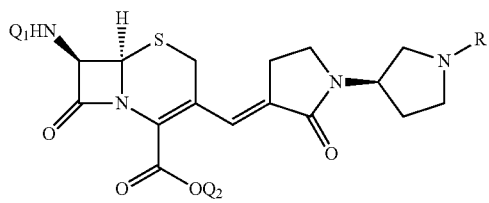

(5)

wherein $Q_1$ and $Q_2$ independently of each other represents silyl group or wherein $Q_1$ represents a hydrogen atom and $Q_2$ represents a silyl group and R represents a 5-methyl-2-oxo-[1,3]-dioxol-4-ylmethoxycarbonyl group.

Objectives of the invention are further obtained by a compound of the formula (5) or (7) obtained by a reaction comprising the steps:

(a) reacting a compound of the formula (3)

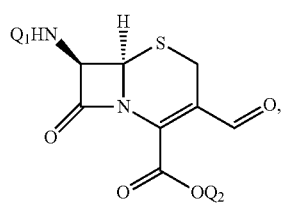

(3)

wherein $Q_1$ and $Q_2$ independently of each other represents a silyl group or wherein $Q_1$ represents a hydrogen atom and $Q_2$ represents a silyl group, with a compound of the formula (4)

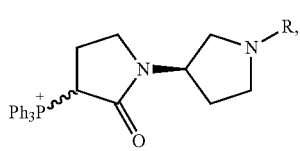

(4)

wherein R represents a 5-methyl-2-oxo-[1,3]-dioxol-4-yl-methoxycarbonyl group, to produce a compound of the formula (5)

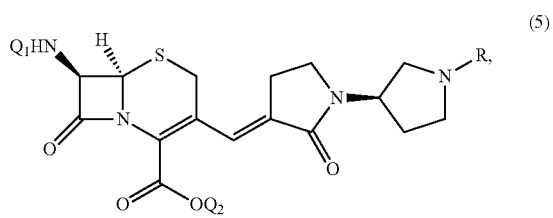

(5)

or (b) reacting the compound of the formula (5) with a compound of the -formula (6)

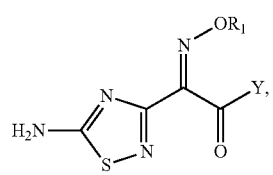

(6)

wherein $R_1$ represents a hydroxy-protective group and Y represents an activating functionality, wherein after removal of the protective group, if $Q_1$ represents a silyl group, to produce a compound of the formula (7)

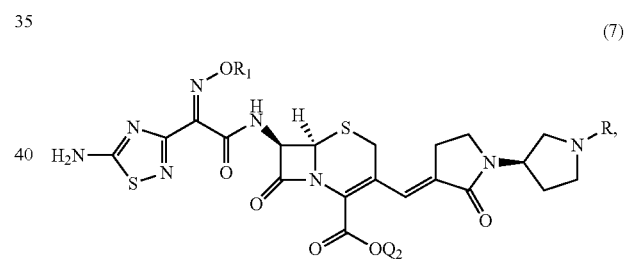

(7)

Objectives of the invention are also obtained by a method of using a compound of the formula (5)

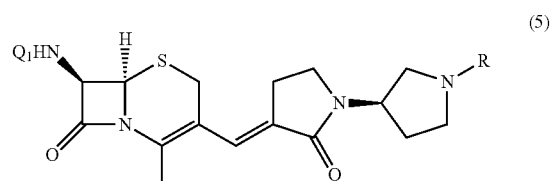

(5)

wherein $Q_1$ and $Q_2$ independently of each other represents a silyl group or wherein $Q_1$ represents a hydrogen atom and $Q_2$ represents a silyl group and R represents a 5-methyl-2-oxo-[1,3]-dioxol-4-ylmethoxycarbonyl group for the production of a compound of the formula (1)

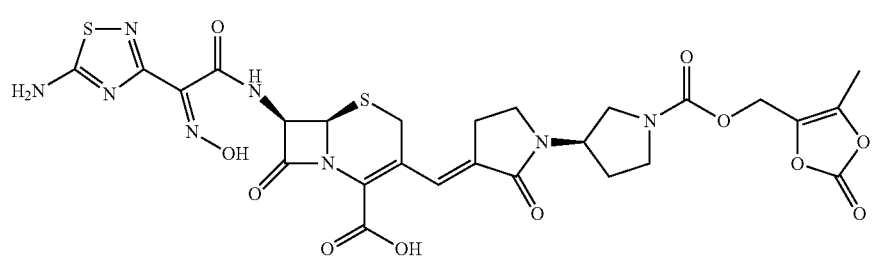

(1)

comprising the step of
(b) reacting the compound of the formula (5) with a compound of the formula (6)

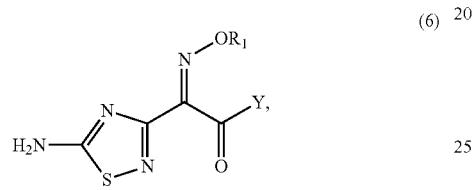

(6)

wherein $R_1$ represents a hydroxy-protective group and Y represents an activating functionality, wherein after optional removal of the protective group, if $Q_1$ represents a silyl group, to produce a compound of the formula (7)

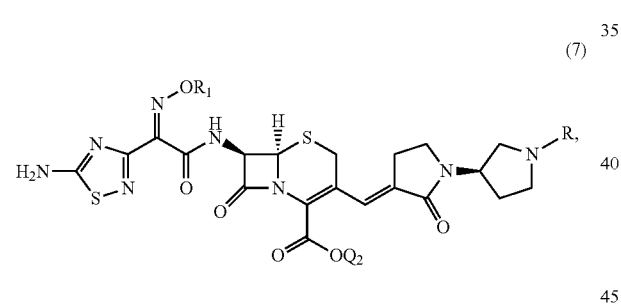

(7)

and (c) converting the compound of formula (7) into the compound of the formula (1).

DETAILED DESCRIPTION OF THE INVENTION

The present invention accordingly relates to a method for the production of a compound of the general formula (1)

comprising at least the following steps (a), (b) and (c):
(a) reaction of a compound of the general formula (3)

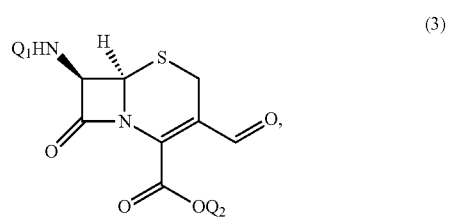

(3)

wherein $Q_1$ and $Q_2$ independently of each other represents a hydrogen atom or a silyl group, in particular wherein Q1 and Q2 independently of each other represents a silyl group or wherein Q1 represents a hydrogen atom and Q2 represents a silyl group, with a compound of the general formula (4)

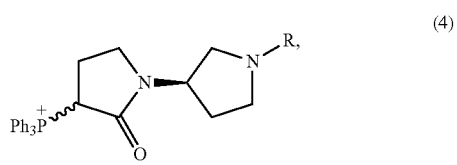

(4)

wherein R represents a 5-methyl-2-oxo-[1,3]-dioxol-4-ylmethoxycarbonyl group,

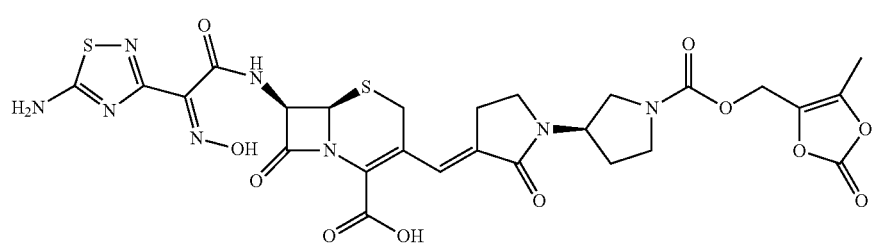

(1)

to give a compound of the general formula (5)

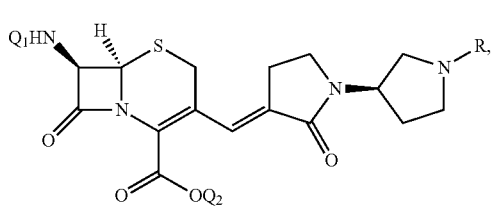

(5)

wherein $Q_1$, $Q_2$ and R are as defined above;
(b) reaction of the compound of the general formula (5) with a compound of the general formula (6)

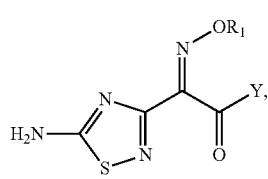

(6)

wherein $R_1$ represents a hydroxy-protective group and Y represents an activating functionality,
where appropriate after removal of the protective group, if $Q_1$ represents a silyl group,
to give a compound of the general formula (7)

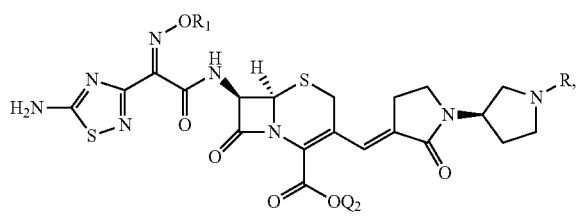

(7)

wherein $R_1$, $Q_2$ and R are as defined above; and
(c) conversion of the compound of the general formula (7) into the compound of the general formula (1).

It has been found, surprisingly, that the compound of the formula (4) wherein R represents a 5-methyl-2-oxo-[1,3]-dioxol 4-ylmethoxycarbonyl group can be used directly in step (a). It would be expected that the ester bond of the medocaril radical would show greater instability under the basic conditions of this step.

The method according to the invention includes at least steps (a), (b) and optionally (c). The method according to the invention can moreover also include further steps, for example protective group operations. In this context, it is possible according to the invention for these further steps to be carried out before or after steps (a), (b) and (c). It is likewise possible, however, for the further steps to be carried out between steps (a) and (b) or between steps (b) and (c).

The method according to the invention makes possible the production of the compound of the general formula (1) in a simple manner and in a high purity.

The method according to the invention includes step (a), i.e. the reaction of a compound of the general formula (3)

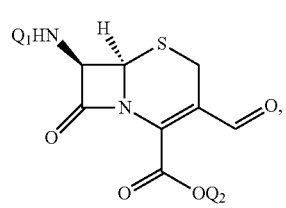

(3)

wherein $Q_1$ and $Q_2$ independently of each other represents a hydrogen atom or a silyl group, in particular wherein Q1 and Q2 independently of each other represents a silyl group or wherein Q1 represents a hydrogen atom and Q2 represents a silyl group,
with a compound of the general formula (4)

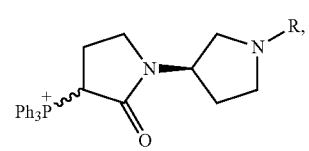

(4)

wherein R represents a 5-methyl-2-oxo-[1,3]-dioxol-4-yl-methoxycarbonyl group (DMDO),
to give a compound of the general formula (5)

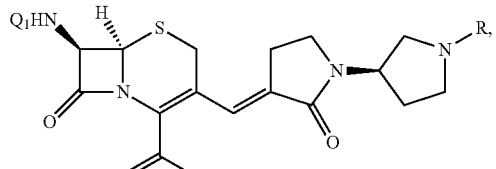

(5)

wherein $Q_1$, $Q_2$ and R are as defined above.

According to the invention, the reaction according to step (a) can be carried out in any manner known to the person skilled in the art. In this reaction, the compound of the general formula (3) is reacted with the phosphonium salt of the general formula (4). The reaction is carried out according to the invention in the presence of a base, with the formation of the compound of the general formula (5).

Suitable reaction conditions and solvent systems are described, for example, in WO 95/29182 on page 26, second paragraph to page 27, to the last-but-one paragraph inclusive, and in Example 31 on page 42 in WO 95/29182.

The reaction according to step (a) can be carried out according to the invention, for example, in the presence of a silylating agent and/or an epoxide, in particular in the presence of BSA and/or propylene oxide.

The present invention therefore also relates to a method for the production of a compound of the general formula (1) as described above, wherein step (a) is carried out in the presence of a silylating agent and an epoxide.

According to preferred embodiments, the present invention also relates to a method for the production of a compound of the general formula (1) as described above, wherein the silylating agent is BSA or wherein the epoxide is propylene oxide.

The methods according to the invention moreover include a step (b), i.e. the reaction of the compound of the general formula (5) with a compound of the general formula (6)

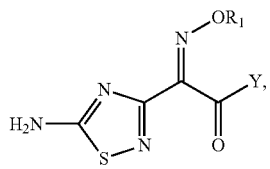

wherein R₁ represents a hydroxy-protective group and Y represents an activating functionality,
where appropriate after removal of the protective group, if Q₁ represents a silyl group,
to give a compound of the general formula (7)

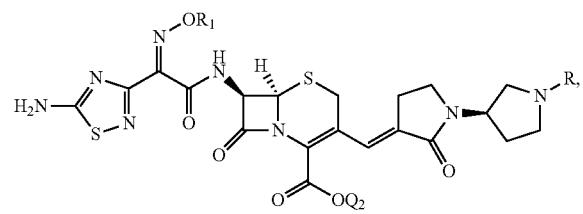

wherein $R_1$, $Q_2$ and R are as defined above.

According to step (b) of the method according to the invention, the compound of the general formula (5) is acylated with the compound of the general formula (6).

According to the invention, Y is an activating functionality, such as, for example, a halide, suitable halides being disclosed, for example, in J. Antibiotics 37:557-571, 1984, a mixed anhydride, suitable mixed anhydrides being disclosed, for example, in Yakugaku Zasshi 110 (9) 658-664, 1990, or a group chosen from the groups (s), (t) and (u):

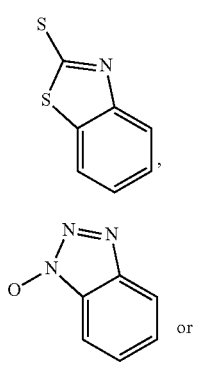

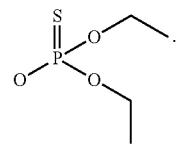

In this context, the reaction according to step (b) of the method according to the invention can in principle be carried out in any manner known to the person skilled in the art.

Suitable reaction conditions and solvent systems are described, for example, in EP 37380 A2 from page 8, line 16 to page 9, line 5.

According to the invention, it is preferable, for the reaction according to step (b), for the compound of the general formula (5) to be dissolved by silylation or salt formation and, after the acylation with the compound of the general formula (6) has been carried out, for the protective groups to be split off in one step.

In this case, in the context of the present invention step (b) can be carried out without intermediate isolation or in a one-pot process.

According to a preferred embodiment, the present invention therefore also relates to a method for the production of a compound of the general formula (1) as described above, wherein for the reaction according to step (b), the compound of the general formula (5) is dissolved by silylation or salt formation and, after acylation with the compound of the general formula (6) has been carried out, the protective groups are split off in one step.

According to a further embodiment, the present invention also relates to a method for the production of a compound of the general formula (1) as described above, wherein step (b) is carried out without intermediate isolation or in a one-pot process.

The method according to the invention can also additionally include a step (c), in addition to steps (a) and (b). According to step (c), the conversion of the general formula (7) into the compound of the general formula (1) is carried out, where appropriate after removal of the protective group, if Q₂ represents a silyl group.

It has been found, surprisingly, that by means of this method according to the invention a reduction in the number of intermediate stages isolated can be obtained in the production of compound of the general formula (1), in particular of ceftobiprole medocaril, which in the end leads to higher overall yields and as a consequence more favorable production costs.

The compounds obtained by the method according to the invention are distinguished, inter alia, by a high purity.

According to a further aspect, the present invention also relates to a compound of the general formula (1)

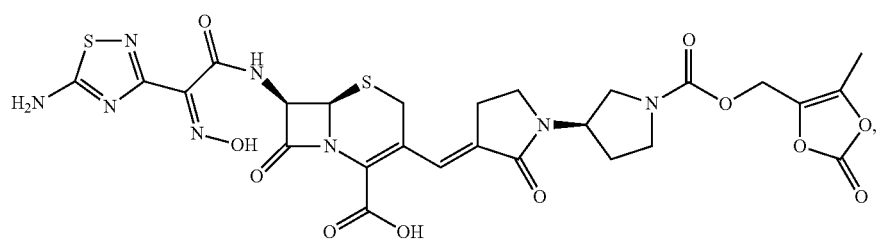

wherein the compound is obtainable by a method as described above.

The present invention also relates to novel intermediates of the synthesis. According to a further aspect, the present invention thus relates to a compound of the general formula (5)

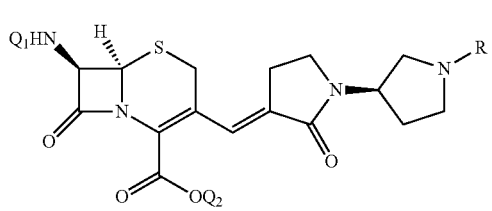

wherein $Q_1$ and $Q_2$ independently of each other represents a hydrogen atom or a silyl group and R represents a 5-methyl-2-oxo-[1,3]-dioxol-4-ylmethoxycarbonyl group, in particular wherein Q1 and Q2 independently of each other represents a silyl group or wherein Q1 represents a hydrogen atom and Q2 represents a silyl group, and salts thereof, in particular organic amine salts, such as e.g. the dicyclohexylamine salt from Example 3, or in particular salts with strong organic acids, such as the trifluoroacetic acid salt or the tosylate or mesylate.

According to the invention, R can represent a 5-methyl-2-oxo-[1,3]-dioxol-4-ylmethoxycarbonyl group. According to a further embodiment, the present invention accordingly relates to a compound of the general formula (5) as described above, wherein $Q_1$ represents a trimethylsilyl group or a hydrogen atom and Q2 represents a trimethylsilyl group and R represents a 5-methyl-2-oxo-[1,3]-dioxol-4-ylmethoxycarbonyl group.

The present invention also relates to compounds of the general formula (5) or of the general formula (7) obtainable by a reaction according to one of steps (a) or (b) as described above.

The compound of the general formula (5) is an essential intermediate stage of the method according to the invention and makes possible the simple synthesis sequence of the method according to the invention.

The present invention therefore also relates to the use of a compound of the general formula (5) as described above for the production of a compound of the general formula (1). The present invention moreover also relates to the use of a compound of the general formula (5) as described above for the production of a compound of the general formula (1).

The present invention is explained in more detail in the following with the aid of examples.

EXAMPLES

1. Example (6R,7R)-7-Amino-3[E-(R)-1'-(5-methyl-2-oxo-[1,3]-dioxol-4-ylmethoxycarbonyl)-2-oxo-[1,3']bipyrrolidinyl-3-ylidenemethyl]-8-oxo-5-thia-1-aza-bicyclo[4.2.0]oct-2-ene-2-carboxylic acid

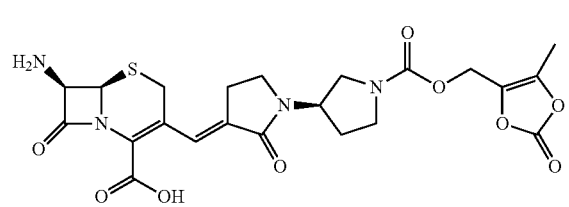 [SMILES: Cc1oc(=O)oc1COC(=O)N1CC[C@@H](N2CC/C(=C\C3=C(C(=O)O)N4C(=O)[C@@H](N)[C@H]4SC3)C2=O)C1]

1.95 g of 7-amino-3-formyl-ceph-3-em-4-carboxylate were dissolved in 13.0 ml of bis(trimethylsilyl)-acetamide and 23 ml of propylene oxide. 6.8 g of (1R/S,3'R)-(1'-(5-methyl-2-oxo-[1,3]-dioxol-4-ylmethoxycarbonyl)-2-oxo-[1,3']bipyrrolidinyl-3-yl)-triphenylphosphonium bromide were then metered in slowly in portions at 1° C. The mixture was subsequently stirred at 1° C. until the starting material has reacted, and thereafter the reaction mixture was stirred into 80 ml of isopropanol. The precipitate was filtered off and washed with isopropanol and methanol. After drying in vacuo, the desired product was obtained in the form of a powder.

Weight: 3.30 g $^1$H-nmr (DMSO-$d_6$) δ 2.03 (m, 2H), 2.14 (s, 3H), 2.8-3.2 (m, 2H), 3.2-3.6 (m, 6H), 3.82 (ABq, J=17.4 Hz, 2H), 4.60 (m, 1H), 4.80 (d, 1H, J=5.0 Hz), 4.90 (s, 2H), 5.00 (d, 1H, J=5.0 Hz), 7.22, (s, 1H)

MS-ESI negative mode: 519.0 (M-H, 70%)

IR (golden gate, cm$^{-1}$): 1815, 1782, 1701, 1674, 1411, 1365

2. Example (6R,7R)-7-Ammonium-3[E-(R)-1'-(5-methyl-2-oxo-[1,3]-dioxol-4-ylmethoxycarbonyl)-2-oxo-[1,3']bipyrrolidinyl-3-ylidenemethyl]-8-oxo-5-thia-1-aza-bicyclo[4.2.0]oct-2-ene-2-carboxylic acid p-toluenesulfonate

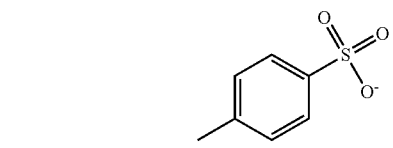

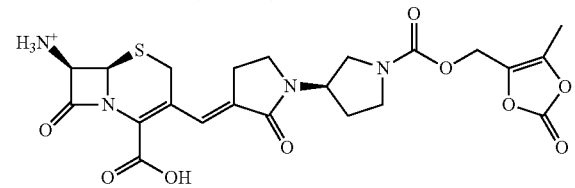

200 mg of (6R,7R)-7-amino-3[E-(R)-1'-(5-methyl-2-oxo-[1,3]-dioxol-4-ylmethoxycarbonyl)-2-oxo-[1,3']bipyrrolidinyl-3-ylidenemethyl]-8-oxo-5-thia-1-aza-bicyclo[4.2.0]oct-2-ene-2-carboxylic acid were dissolved in 3 ml of methanol with addition of 95 mg of p-toluenesulfonic acid monohydrate and precipitated by the addition of 12 ml of isopropanol. The precipitate was filtered and washed with isopropanol.

Weight: 218 mg $^1$H-nmr (DMSO-d$_6$) δ 2.03 (m, 2H), 2.14 (s, 3H), 2.27 (s, 3H), 2.75-3.2 (m, 2H), 3.2-3.6 (m, 6H), 3.96 (ABq, J=17.4 Hz, 2H), 4.60 (m, 1H), 4.91 (s, 2H), 5.20 (d, 1H, J=5.0 Hz), 5.24 (d, 1H, J=5.0 Hz), 7.10 & 7.46 (AA'BB'm, 4H), 7.28 (s, 1H)

MS-ESI negative mode: 519.0 (M-H, 100%)
IR (golden gate, cm$^{-1}$): 1785, 1684, 1629, 1429, 1369

The product can also be prepared directly from the reaction mixture by desilylation with isopropanol in the presence of p-toluenesulfonic acid.

3. Example

Dicyclohexylammonium (6R,7R)-7-amino-3[E-(R)-1'-(5-methyl-2-oxo-[1,3]-dioxol-4-ylmethoxycarbonyl)-2-oxo-[1,3']bipyrrolidinyl-3-ylidenemethyl]-8-oxo-5-thia-1-aza-bicyclo[4.2.0]oct-2-ene-2-carboxylate

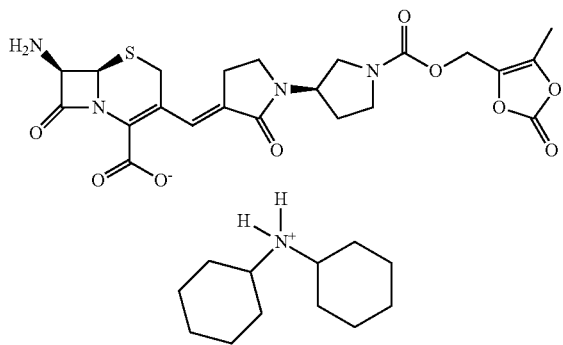

200 mg of (6R,7R)-7-amino-3[E-(R)-1'-(5-methyl-2-oxo-[1,3]-dioxol-4-ylmethoxycarbonyl)-2-oxo-[1,3']bipyrrolidinyl-3-ylidenemethyl]-8-oxo-5-thia-1-aza-bicyclo[4.2.0]oct-2-ene-2-carboxylic acid were dissolved in 3 ml of methanol with addition of 95 mg of p-toluenesulfonic acid monohydrate and precipitated by the addition of 12 ml of isopropanol.

$^1$H-nmr (DMSO-d$_6$) δ 1.0-1.4 (m, 10H), 1.4-1.8 (m, 6H), 1.8-2.1 (m, 6H), 2.14 (s, 3H), 2.7-3.15 (m, 4H), 3.15-3.68 (m, 6H), 3.68 (ABq, J=16.8 Hz, 2H), 4.59 (m, 2H), 4.89 (m, 3H), 7.33 (s, 1H)

MS-ESI negative mode: 519.0 (M-H, 50%)
IR (golden gate, cm$^{-1}$): 2934, 2859, 1819, 1756, 1704, 1674, 1631, 1575

4. Example (6R,7R)-7-[(Z)-2-(5-Amino-[1,2,4]thiadiazol-3-yl)-2-triphenylmethyloxyimino-acetylamino]-8-oxo-3-[(E)-(R)-2-oxo-1'-(5-methyl-2-oxo-[1,3]-dioxol-4-ylmethoxycarbonyl)-[1,3']bipyrrolidinyl-3-ylidenemethyl]-5-thia-1-aza-bicyclo[4.2.0]oct-2-ene-2-carboxylic acid

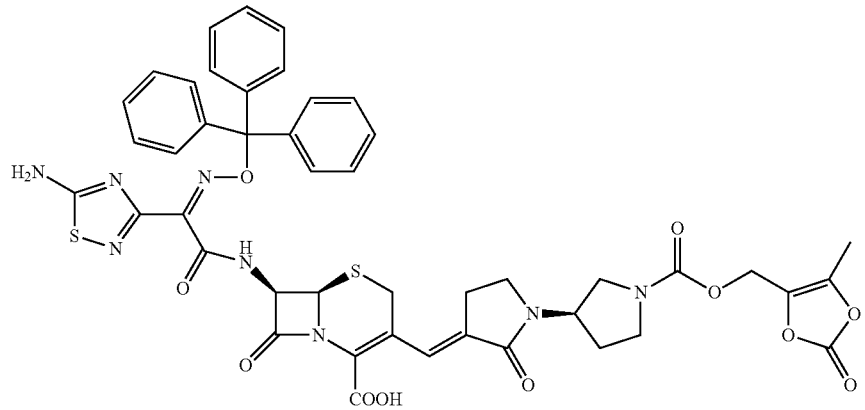 [SMILES: Cc1oc(=O)oc1COC(=O)N1CC[C@@H](N2CC/C(=C\C3=C(C(=O)O)N4C(=O)[C@@H](NC(=O)/C(=N\OC(c5ccccc5)(c5ccccc5)c5ccccc5)c5nsc(N)n5)[C@H]4SC3)C2=O)C1]

0.5 g of (6R, 7R)-7-amino-3[E-(R)-1'-(5-methyl-2-oxo-[1,3]-dioxol-4-ylmethoxycarbonyl)-2-oxo-[1,3']bipyrrolidinyl-3-ylidenemethyl]-8-oxo-5-thia-1-aza-bicyclo[4.2.0]oct-2-ene-2-carboxylic acid were dissolved in 20 ml of dichloromethane at 0°. 0.7ml of bis(trimethylsilyl)acetamide were then added and 0.46 g of 2-trityloxyimino-2-(5-amino-1,2,4-thiadiazol-3-yl)-acetic acid chloride hydrochloride (J. Antibiotics 37:557-571, 1984) were metered in portions. The mixture was poured onto 15 ml of water/15 ml of MeOH and the phases were separated. The water phase was washed once again with 15 ml of dichloromethane and the combined organic phases were dried over sodium sulfate and concentrated in vacuo.

Weight: 0.93 g $^1$H-nmr (DMSO-d$_6$) δ 1.9-2.05 (m, 2H), 2.10 (s, 3H), 2.8-3.1 (m, 2H), 3.2-3.5 (m, 6H), 3.84 (ABq, 2H, J=17.8 Hz), 4.55 (m, 1H), 4.86 (s, 2H), 5.22 (d, 1H, J=5.1 Hz), 6.02 (dd, 1H, J1=5.1 Hz, J2-8.8 Hz), 7.1-7.3 (m, 16H), 8.08 (br s, 2H), 9.90 (d, 1H, J=8.8 Hz)

IR (golden gate, cm$^{-1}$): 1814, 1781, 1663, 1619, 1526

5. Example

Ceftobiprole Medocaril

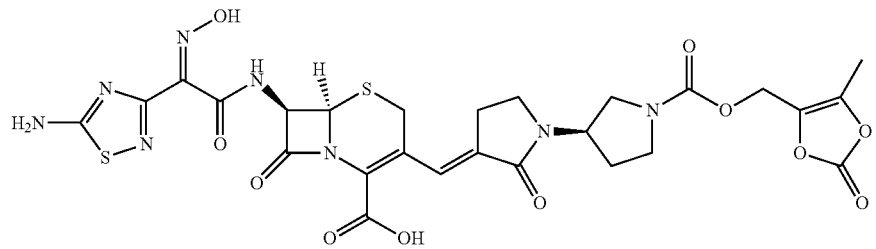 [SMILES: Cc1oc(=O)oc1COC(=O)N1CC[C@@H](N2CC/C(=C\C3=C(C(=O)O)N4C(=O)[C@@H](NC(=O)/C(=N\O)c5nsc(N)n5)[C@H]4SC3)C2=O)C1]

90 mg of (6R,7R)-7-[(Z)-2-(5-amino-[1,2,4]-thiadiazol-3-yl)-2-triphenylmethyloxyiminoacetyl-amino]-8-oxo-3-[(E)-(R)-2-oxo-1'-(5-methyl-2-oxo-1,3-dioxol-4-ylmethoxycarbonyl)-[1,3']bi-pyrrolidinyl-3-ylidenemethyl]-5-thia-1-aza-bicyclo[4.2.0]oct-2-ene-2-carboxylic acid were dissolved in 10 ml of dichloromethane, 0.5 ml of triethylsilane and 2 ml of trifluoroacetic acid and stirred at room temperature. After 30 minutes the mixture is added dropwise to 150 ml of diethyl ether. The precipitate is filtered, washed with diethyl ether and dried in vacuo.

Weight: 60 mg $^1$H-nmr (DMSO-$d_6$) δ 1.9-2.1 (m, 2H), 2.14 (s, 3H), 2.8-3.2 (m, 2H), 3.2-3.6 (m, 6H), 3.84 (ABq, 2H, J=18.9 Hz), 4.60 (m, 1H), 4.90 (s, 2H), 5.16 (d, 1H, J=4.8 Hz), 5.85 (dd, 1H, J1=4.8 Hz, J2=8.5 Hz), 7.22 (s, 1H), 8.05 (br s, 2H), 9.47 (d, 1H, J=8.5 Hz), 11.91 (s, 1H)

IR (golden gate, cm$^{-1}$): 1780, 1664, 1624, 1527, 1428, 1366

The invention claimed is:

1. A method for the production of a compound of the formula (1)

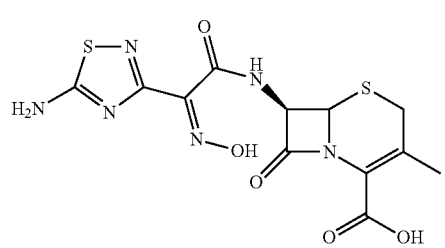 (1)

comprising at least the following steps (a) and (b):

(a) reacting a compound of the formula (3)

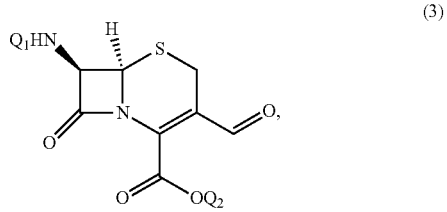 (3)

wherein $Q_1$ and $Q_2$ independently of each other represent a silyl group or wherein $Q_1$ represents a hydrogen atom and $Q_2$ represents a silyl group, with a compound of the formula (4)

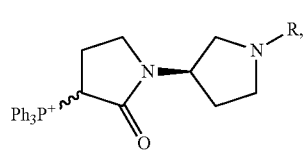 (4)

wherein R represents a 5-methyl-2-oxo-[1,3]-dioxol-4-yl-methoxycarbonyl group, to produce a compound of the formula (5)

and (5)

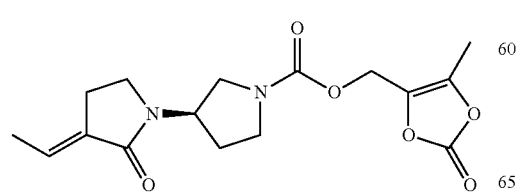
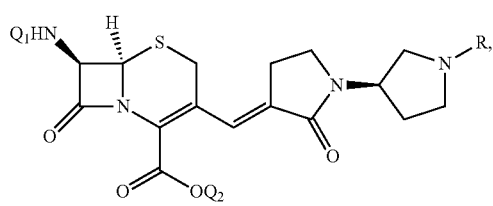

(b) reacting the compound of the formula (5) with a compound of the formula (6)

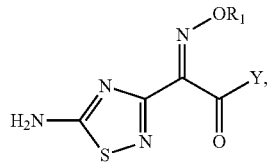

wherein $R_1$ represents a hydroxy-protective group and Y represents an activating functionality, wherein after removal of the protective group, if $Q_1$ represents a silyl group, to produce a compound of the formula (7)

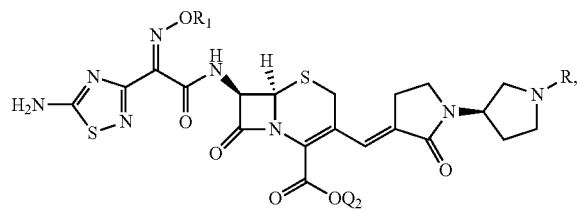

and (c) converting the compound of the formula (7) into the compound of the formula (1), wherein step (a) is carried out in the presence of a silylating agent and an epoxide.

2. The method according to claim 1, wherein the silylating agent is bis(trimethylsilyl)acetamide.

3. The method according to claim 2, wherein the epoxide is propylene oxide.

4. The method according to claim 1, wherein for the reaction according to step (b) the compound of the formula (5) is dissolved by silylation or salt formation, and when the acylation with the compound of the formula (6) has been carried out, the protective groups are split off in one step.

5. A compound of the formula (5)

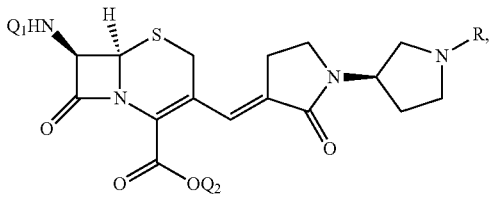

wherein $Q_1$ and $Q_2$ independently of each other represents a silyl group or wherein $Q_1$ represents a hydrogen atom and $Q_2$ represents a silyl group and R represents a 5-methyl-2-oxo-[1,3]-dioxol-4-ylmethoxycarbonyl group.

6. The compound according to claim 5, wherein $Q_1$ represents a trimethylsilyl group.

7. The compound according to claim 5, wherein the compound is present as a salt with an organic amine or as an acid addition salt.

8. A method of using a compound of the formula (5)

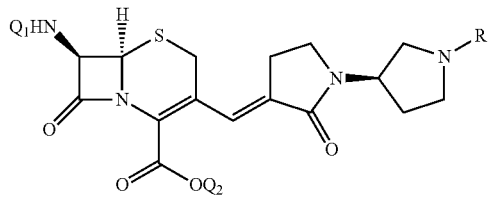

wherein $Q_1$ and $Q_2$ independently of each other represent a silyl group or wherein $Q_1$ represents a hydrogen atom and $Q_2$ represents a silyl group and R represents a 5-methyl-2-oxo-[1,3]-dioxol-4-ylmethoxycarbonyl group for the production of a compound of the formula (1)

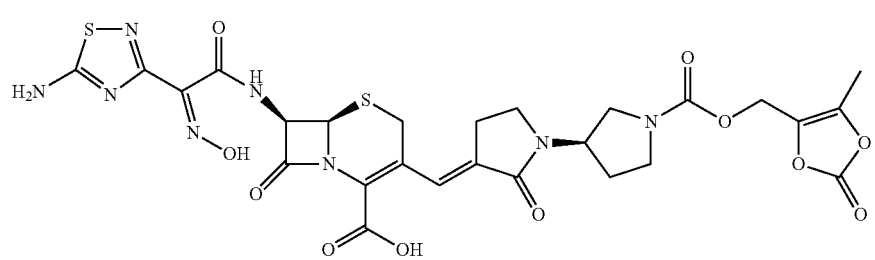

comprising the step of
(b) reacting the compound of the formula (5) with a compound of the formula (6)

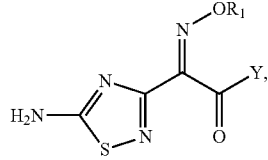
(6)

wherein $R_1$ represents a hydroxy-protective group and Y represents an activating functionality, wherein after optional removal of the protective group, if $Q_1$ represents a silyl group, to produce a compound of the formula (7)

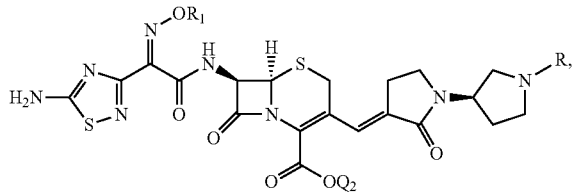
(7)

and (c) converting the compound of formula (7) into the compound of the formula (1).

* * * * *